US012751699B2

(12) United States Patent
Ozdoganlar et al.

(10) Patent No.: US 12,751,699 B2
(45) Date of Patent: Oct. 6, 2026

(54) SAMPLING SWABS AND METHODS OF MAKING THE SAME

(71) Applicant: Carnegie Mellon University, Pittsburgh, PA (US)

(72) Inventors: O. Burak Ozdoganlar, Sewickley, PA (US); Yusuf Senturk, Pittsburgh, PA (US); Toygun Cetinkaya, Pittsburgh, PA (US); Ant Yucesoy, Pittsburgh, PA (US); Ali Gurer, Pittsburgh, PA (US); Lisha White, Pittsburgh, PA (US); Ezgi Yalcintas, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 365 days.

(21) Appl. No.: 17/920,660

(22) PCT Filed: Apr. 23, 2021

(86) PCT No.: PCT/US2021/028881
§ 371 (c)(1),
(2) Date: Oct. 21, 2022

(87) PCT Pub. No.: WO2021/217025
PCT Pub. Date: Oct. 28, 2021

(65) Prior Publication Data

US 2023/0141251 A1 May 11, 2023

Related U.S. Application Data

(60) Provisional application No. 63/014,595, filed on Apr. 23, 2020.

(51) Int. Cl.
*A61B 10/00* (2006.01)
*A61B 10/02* (2006.01)

(52) U.S. Cl.
CPC .......... *A61B 10/02* (2013.01); *A61B 10/0045* (2013.01); *A61B 2010/0216* (2013.01)

(58) Field of Classification Search
CPC ................ A61B 10/02; A61B 10/0045; A61B 2010/0216; A61B 2010/0074;
(Continued)

(56) References Cited

U.S. PATENT DOCUMENTS 4,746,238 A * 5/1988 Levine .................... A61F 13/38
401/196
8,323,211 B2 12/2012 Larkin
(Continued)

FOREIGN PATENT DOCUMENTS

CN 1280865 A * 1/2001 ............ A63B 59/52
CN 201108537 Y * 9/2008
(Continued)

OTHER PUBLICATIONS

International Search Report and Written Opinion dated Aug. 13, 2021 for corresponding PCT Application No. PCT/US2021/028881.

*Primary Examiner* — Robert R Raevis
(74) *Attorney, Agent, or Firm* — Michael E. Dukes; Dentons Cohen & Grigsby, P.C.

(57) ABSTRACT

A device to collect a biological sample may generally include an elongated rod having a handle and terminating in a tip; and a core and a plurality of projections extending in a radial direction from a surface of the core. The projections may have curved geometric pattern, such as a sinusoidal pattern, a circular arc pattern, and/or a helical pattern, for example. The device may include a layer of fibers disposed on a surface of the projections by flocking. Method of making and using the device are also described.

18 Claims, 19 Drawing Sheets

(58) Field of Classification Search
CPC ........ A61B 10/0051; A61B 1010/0054; B01L 3/5029; A61F 13/36; A61F 13/38; G01N 2001/028
USPC ...... 73/863, 864.71, 864.73; 600/573; 604/1
See application file for complete search history.

(56) References Cited

U.S. PATENT DOCUMENTS

| | | | | |
|---|---|---|---|---|
| 2017/0065261 | A1 | 3/2017 | Ching et al. | |
| 2023/0141251 | A1* | 5/2023 | Ozdoganlar ....... | A61B 10/0051 73/863 |

FOREIGN PATENT DOCUMENTS

| | | | | | |
|---|---|---|---|---|---|
| CN | 202277390 | U | * | 6/2012 | |
| CZ | 273595 | A3 | * | 7/1996 | |
| DE | 60127608 | T2 | * | 12/2007 | ............... A46B 5/00 |
| DE | 102016121617 | A1 | * | 5/2018 | |
| DE | 102017211242 | A1 | * | 1/2019 | |
| EP | 3009114 | A1 | * | 4/2016 | ............ A61F 11/006 |
| JP | 2001120699 | | * | 5/2001 | |
| JP | 2001120699 | A | * | 5/2001 | |
| JP | 2019534449 | A | * | 11/2019 | |
| WO | WO-2019099056 | A1 | * | 5/2019 | ............ A61F 11/006 |

* cited by examiner

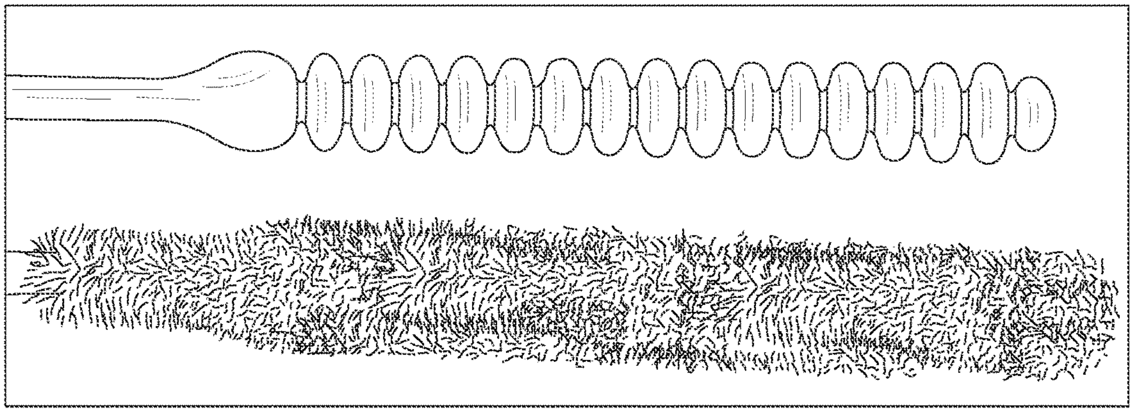
FIG. 1
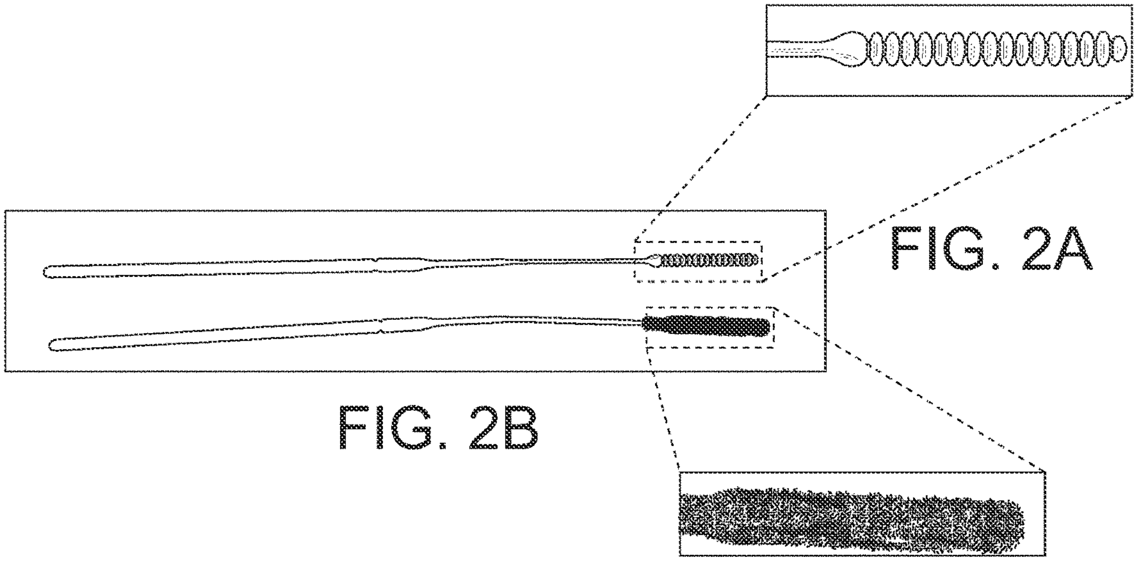
FIG. 2A
FIG. 2B
FIG. 2C
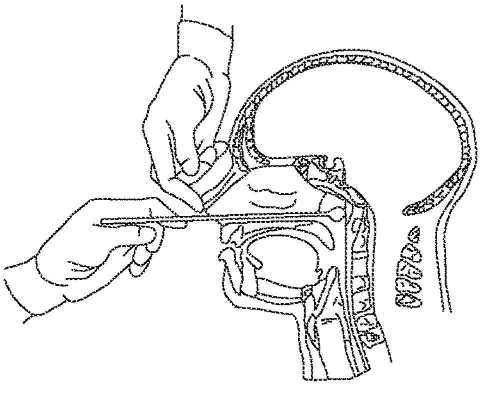
FIG. 3

SAMPLING SWABS AND METHODS OF MAKING THE SAME

CROSS-REFERENCE TO RELATED APPLICATIONS

This application is a U.S. national stage filing under 35 U.S.C. § 371 of International Application No. PCT/US2021/028881, filed on Apr. 23, 2021, which claims the benefit of U.S. Provisional Application No. 63/014,595, filed Apr. 23, 2020, the entire contents of which is incorporated herein by reference.

TECHNICAL FIELD

This disclosure generally relates to sampling swabs, such as swabs used to collect biological samples, as well as methods of making and using the same.

BACKGROUND

There is an unmet need for the supply of swabs in the United States. Swabs are intended for various uses in healthcare, such as, collecting specimens from patients and applying medications. During COVID-19, swabs' role in the U.S. healthcare system became even more important because swabs are used in COVID-19 diagnostic test kits. The shortage of swabs is hampering U.S. response to the COVID-19 crisis, and the U.S. healthcare system is struggling to find reliable and FDA-compliant sources of swabs. Not only does this shortage affect the U.S. response to the COVID-19 crisis, but it also disrupts access to other clinical situations that require swabs for proper care. The demand for swabs is expected to grow continuously, and the U.S. market accounts for a large portion of this demand.

U.S. Food and Drug Administration ("FDA") has not defined the term "unmet need" in the context of Emergency Use Authorizations. However, the agency had defined similar terms in other contexts, such as when FDA defined "unmet medical need" as "a condition whose treatment or diagnosis is not addressed adequately by available therapy. An unmet medical need includes an immediate need for a defined population (i.e., to treat a serious condition with no or limited treatment) or a longer-term need for society (e.g., to address the development of resistance to antibacterial drugs)" See *Guidance for Industry: Expedited Programs for Serious Conditions—Drugs and Biologics* (May 2014). An unmet need may be described as "a need that is not addressed adequately by available supply, or a need that includes an immediate need for a defined population or a longer-term need for society."

Based on this definition, there is an unmet need for swabs currently in the United States. First, an unmet need exists because the need for swabs is not adequately addressed by the currently available supply in the United States. In fact, FDA acknowledged this as recently as Dec. 23, 2020, when the agency updated its medical device shortage list, including swabs, such as swabs designated under Product Code KXG, 21 C.F.R. § 880.6025. This shortage list also includes critical products such as ventilators, microbiological specimen collection, transport devices, micro pipettes, and surgical respirators.

The FDA creates this list based on real-world information and notifications it receives from manufacturers regarding "an interruption in the manufacture of the device that is likely to lead to a meaningful disruption in [the] supply of that device in the United States." It is worth noting that the federal Food, Drug, and Cosmetic Act ("FDCA"), defines the term "shortage" as "a period of time when the demand or projected demand for the device within the United States exceeds the supply of the device." FDCA Section 506J(i)(2). Thus, by definition, the fact that swabs are on this list means that the current demand for swabs exceeds the available supply—i.e., an unmet need exists.

Considering that the United States continues to identify an extremely high number of COVID-19 cases each day (more than 230,000 as of Jan. 14, 2021), this unmet need may have potentially devastating effects on the battle against COVID-19. In 2020, clinics that perform COVID-19 tests were forced to shut down because of the lack of swabs, and the shortage of swabs at times contributed to the inability of states and localities to re-open their economies.

Importantly, the swab shortage does not appear to have been resolved. Reports from the industry support the FDA's current understanding of unmet needs for swabs. For example, on Nov. 9, 2020, the Wall Street Journal reported that "doctors and laboratories face shortfalls of the swabs, chemicals and other equipment needed to test patients and process tests . . . ." Because swabs are such a critical component of the U.S. healthcare system, the shortage of swabs affects more than just COVID-19 tests. Accordingly, more efficient and/or cost-effective swabs as well as methods of making the same may be desirable.

SUMMARY

The present invention is directed to more efficient and/or cost-effective swabs as well as methods of making and using the same.

A device to collect a sample according to the present invention may generally include an elongated rod having a handle and terminating in a tip; and a core and a plurality of projections extending in a radial direction from a surface of the core. The projections may have curved geometric pattern, such as a sinusoidal pattern, a circular arc pattern, and/or a helical pattern, for example. The projection may comprise a waveform pattern, such as, a sine wave, a square wave, a triangle wave, a sawtooth wave, and combinations thereof, for example.

The device may include a layer of fibers disposed on a surface of the projections by flocking. The swabs may collect the sample with or without flocked fibers.

A method of making a device to collect a sample according to the present invention may comprise injection molding, 3D printing, Swiss turning, and/or other plastic fabrication processes. The method may comprise making an elongated rod having a handle and terminating in a tip, and a core and a plurality of projections extending in a radial direction from a surface of the core via injection molding and/or 3D printing. The method may comprise applying an adhesive coating to the projections, disposing flocking material to the coated projections, and curing the device coated with the adhesive and flocking material.

A method of using the swabs according to the present invention may comprise collecting a biological sample from a patient or object by contacting the swab and a source of material such that a sample of the material is retained by the swab. The patient may be a human, small animal (e.g., dogs, cats, and other companion animals/household pets such as hamsters and gerbils), laboratory animal (e.g., bovines, porcine species, felines, canines, rodents, and exotic animals), or large animal (e.g., livestock and other large farm animals, as well as equine species and large reptiles). The swab be used to collect biological samples from oral, nasal, ocular, rectal, urethral, or vaginal orifices of the patient. The object may be a surface or fluid potentially contaminated with pathogens and/or microbes.

A method of using the swabs according to the present invention may comprise collecting a sample by contacting a projection according to the present invention and/or a layer of fibers of a flocking material disposed on the projection; storing and transporting a quantity of the collected sample; and releasing a quantity of the collected sample to be analyzed from the projections and/or fibers. The method may comprise rotating the swab in a direction of the projections (e.g., for a right-handed helix or a left-handed helix) to collect the sample. The method may comprise the step of analyzing the quantity of the sample after releasing the sample from the projection and/or fibers.

The swabs according to the present invention may comprise a component of a collection, transport, culture and/or transport kit or device and/or container and/or devices configured to be integrated with the swab and/or tip to provide one or more of sample retention, integrity and/or sterility.

BRIEF DESCRIPTION OF THE FIGURES

The devices and processes described herein may be better understood by considering the following description in conjunction with the accompanying drawings; it being understood that this disclosure is not limited to the accompanying drawings.

FIG. 1 shows a nasopharyngeal swab according to the present invention prior to flocking (top) and after flocking (bottom).

FIGS. 2A-C show a nasopharyngeal swab according to the present invention prior to flocking and after flocking (middle FIG. 2A), an exploded view of the tip prior to flocking (top FIG. 2B), and an exploded view of the tip after flocking (bottom FIG. 2C).

FIG. 3 shows a method of using a nasopharyngeal swab according to the present invention.

DETAILED DESCRIPTION

Figure 4A:
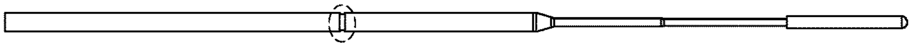
FIGS. 4A-G include a swab according to the present invention comprising an elongated rod comprising a body having a notch and terminating in the tip. The swab may be characterized by a shaft diameter, a tip shaft diameter, a notch diameter, a notch length, a notch fillet radius, a middle section diameter, a projection diameter, a transition-1 length, a transition-2 length, a projection wall angle, a fillet radius, a projection fillet radius, a tip radius, a tip transition fillet radius, and a tip transition length.
Figure 4B:
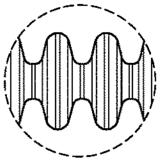
Figure 4C:
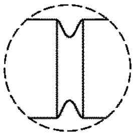
Figure 4D:
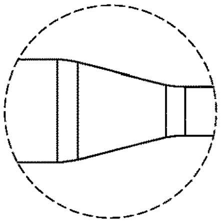
Figure 4E:
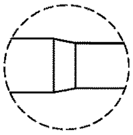
Figure 4F:
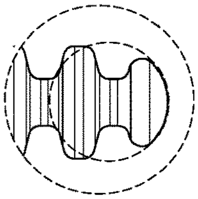
Figure 4G:
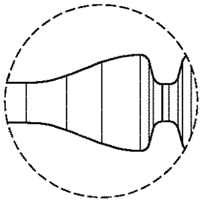
Figure 5A:
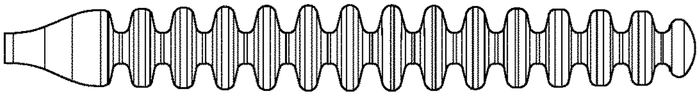
FIGS. 5A-C show swabs according to the present invention having a core diameter of 1 mm, a radial diameter of the projections of 2.75 mm, and a frequency of 13 (i.e., projections having a spacing to 1.43 mm) (FIG. 5A), a frequency of 12 (i.e., projections having a spacing to 1.55 mm) (FIG. 5B), and a frequency of 11 (i.e., projections having a spacing to 1.1.68 mm) (FIG. 5C).
Figure 5B:
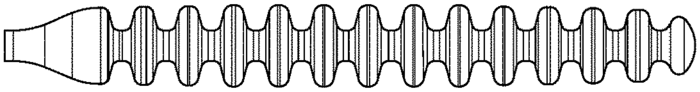
Figure 5C:
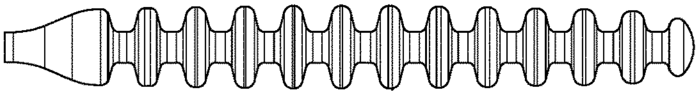
Figures 6A, 6B:
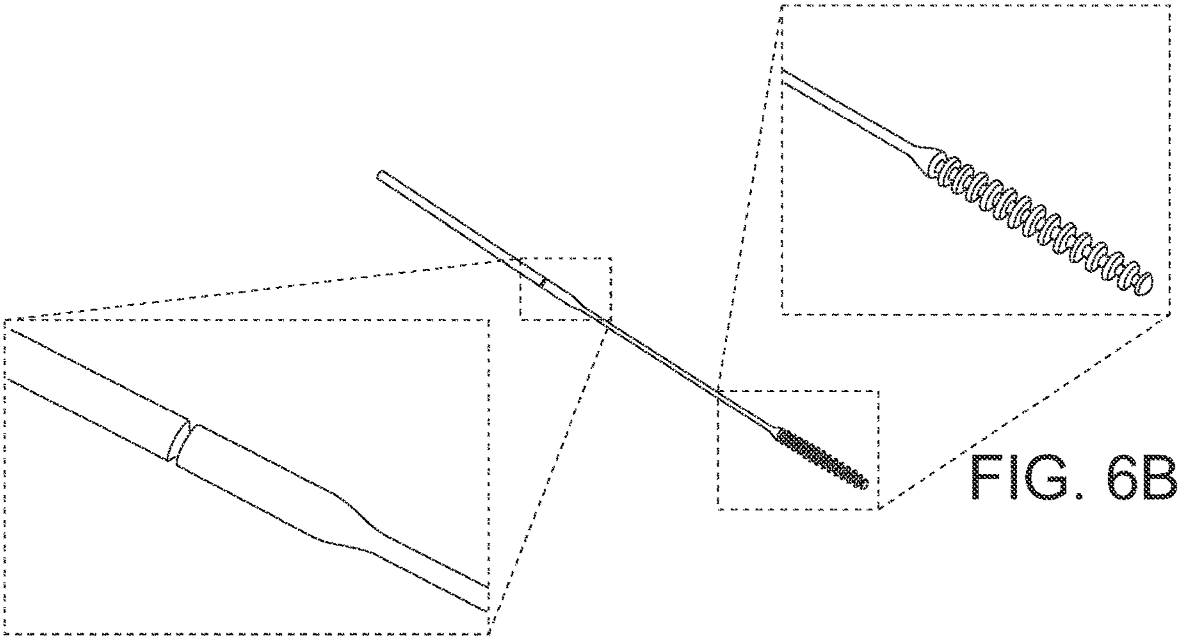
FIGS. 6A-B show a swabs according to the present invention comprising cage-like features to collect the sample.
Figure 7A:
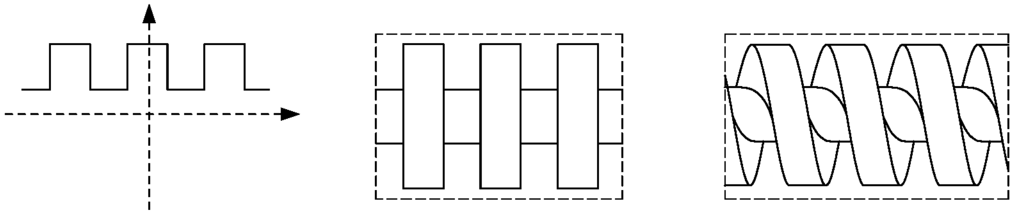
FIGS. 7A-E shows waveforms (left) of the projections according to the present invention including pulse (square, semicircle, sawtooth, sine, and circular pulse) patterns (center) and helical patterns (right).
Figure 7B:
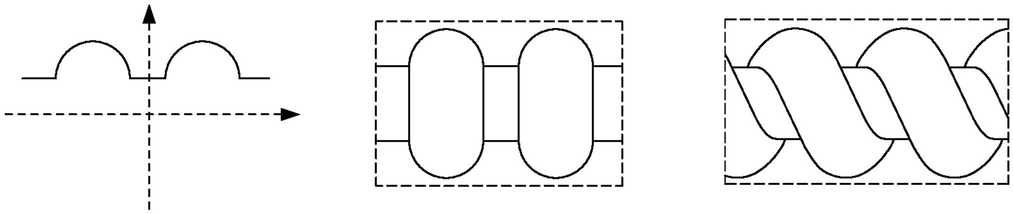
Figure 7C:
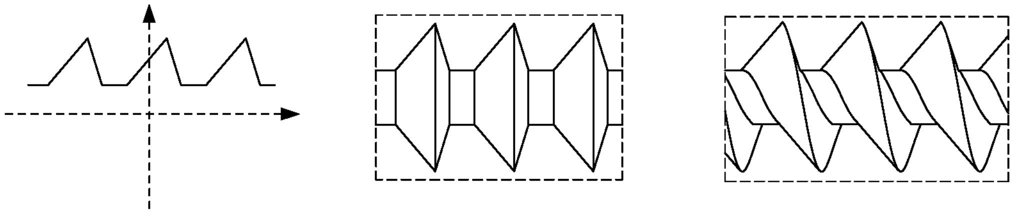
Figure 7D:
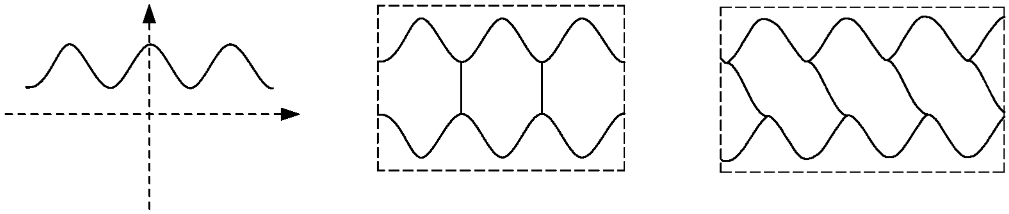
Figure 7E:
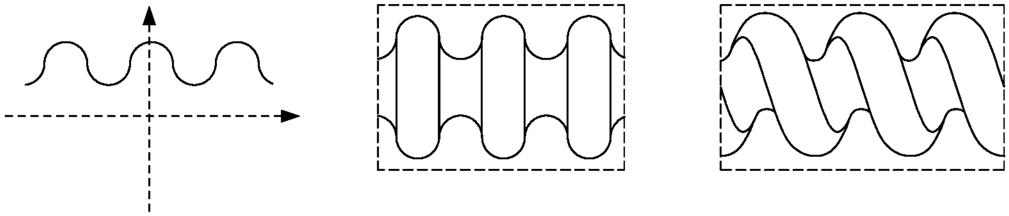
Figure 8A:
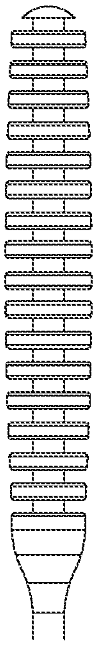
FIGS. 8A-F show swabs according to the present invention having a honey-dipper type tip, including diameters that remain constant, increase from the proximal end to a central portion and decreases from the central portion to the distal end, and increases from the proximal end to the distal end. The swab may have infinite order rotational symmetry about its center longitudinal axis such that the views from the front, back, left, and right are the same. The end views may be the same or different as any of the end views shown in FIGS. 13-15.
Figure 8B:
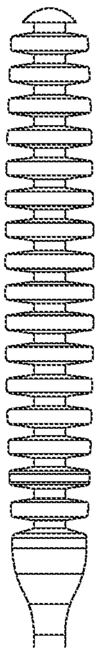
Figure 8C:
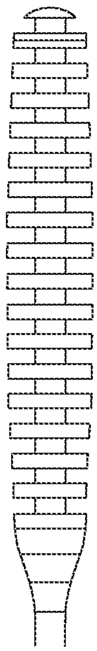
Figure 8D:
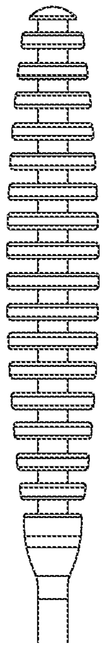
Figure 8E:
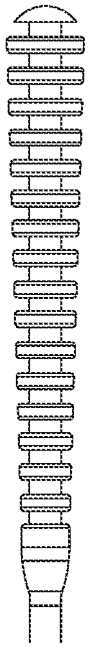
Figure 8F:
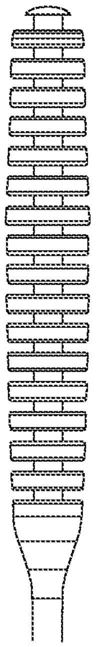
Figure 9A:
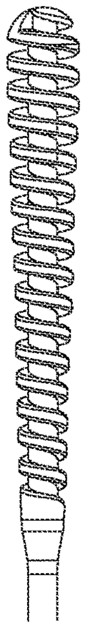
FIGS. 9A-G show swabs according to the present invention having a helical type tip, including an amplitude that remains constant, increase from the proximal end to a central portion and decreases from the central portion to the distal end, and increases from the proximal end to the distal end. The swab may have infinite order rotational symmetry about its center longitudinal axis such that the views from the front, back, left, and right are the same. The end views may be the same or different as any of the end views shown in FIGS. 13-15.
Figure 9B:
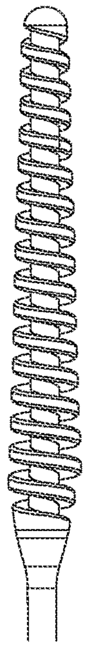
Figure 9C:
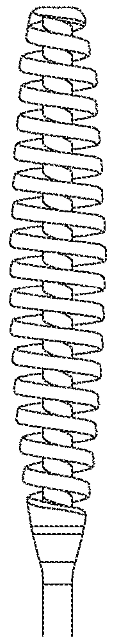
Figure 9D:
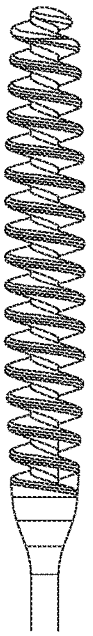
Figure 9E:
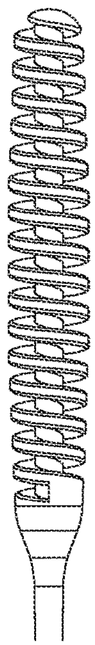
Figure 9F:
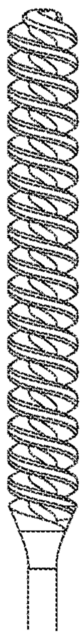
Figure 9G:
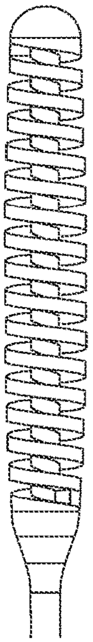

This disclosure generally describes swabs as well as methods of making and using the same. It is understood, however, that this disclosure also embraces numerous alternative features, aspects, and advantages that may be accomplished by combining any of the various features, aspects, and/or advantages described herein in any combination or sub-combination that one of ordinary skill in the art may find useful. Such combinations or sub-combinations are intended to be included within the scope of this disclosure. As such, the claims may be amended to recite any features, aspects, and advantages expressly or inherently described in, or otherwise expressly or inherently supported by, this disclosure. Further, any features, aspects, and advantages that may be present in the prior art may be affirmatively disclaimed. Accordingly, this disclosure may comprise, consist of, consist essentially or be characterized by one or more of the features, aspects, and advantages described herein. As used herein, the term "and/or" includes any and all combinations of one or more of the associated listed items.

All numerical quantities stated herein are approximate, unless stated otherwise. Accordingly, the term "about" may be inferred when not expressly stated. The numerical quantities disclosed herein are to be understood as not being strictly limited to the exact numerical values recited. Instead, unless stated otherwise, each numerical value stated herein is intended to mean both the recited value and a functionally equivalent range surrounding that value. At the very least, and not as an attempt to limit the application of the doctrine of equivalents to the scope of the claims, each numerical value should at least be construed in light of the number of reported significant digits and by applying ordinary rounding processes. Typical exemplary degrees of error may be within 20%, 10%, or 5% of a given value or range of values. Alternatively, and particularly in biological systems, the terms “about” refers to values within an order of magnitude, potentially within 5-fold or 2-fold of a given value. Notwithstanding the approximations of numerical quantities stated herein, the numerical quantities described in specific examples of actual measured values are reported as precisely as possible. Any numerical values, however, inherently contain certain errors necessarily resulting from the standard deviation found in their respective testing measurements.

All numerical ranges stated herein include all sub-ranges subsumed therein. For example, a range of “1 to 10” or “1-10” is intended to include all sub-ranges between and including the recited minimum value of 1 and the recited maximum value of 10 because the disclosed numerical ranges are continuous and include every value between the minimum and maximum values. Any maximum numerical limitation recited herein is intended to include all lower numerical limitations. Any minimum numerical limitation recited herein is intended to include all higher numerical limitations.

All compositional ranges stated herein are limited in total to and do not exceed 100 percent (e.g., volume percent or weight percent) in practice. When multiple components may be present in a composition, the sum of the maximum amounts of each component may exceed 100 percent, with the understanding that, and as those skilled in the art would readily understand, that the amounts of the components may be selected to achieve the maximum of 100 percent.

In the following description, certain details are set forth in order to provide a better understanding of various features, aspects, and advantages the invention. However, one skilled in the art will understand that these features, aspects, and advantages may be practiced without these details. In other instances, well-known structures, methods, and/or processes associated with methods of practicing the various features, aspects, and advantages may not be shown or described in detail to avoid unnecessarily obscuring descriptions of other details of the invention.

The terminology used herein is for the purpose of describing particular examples only and is not intended to be limiting. As used herein, the singular forms “a”, “an”, and “the” may be intended to include the plural forms as well, unless the context clearly indicates otherwise. The terms “comprises”, “comprising”, “including”, “having”, and “characterized by”, are inclusive and therefore specify the presence of stated features, elements, compositions, steps, integers, operations, and/or components, but do not preclude the presence or addition of one or more other features, integers, steps, operations, elements, components, and/or groups thereof. Although these open-ended terms are to be understood as a non-restrictive term used to describe and claim various aspects set forth herein, in certain aspects, the term may alternatively be understood to instead be a more limiting and restrictive term, such as “consisting of” or “consisting essentially of.” Thus, for any given embodiment reciting compositions, materials, components, elements, features, integers, operations, and/or process steps, described herein also specifically includes embodiments consisting of, or consisting essentially of, such recited compositions, materials, components, elements, features, integers, operations, and/or process steps. In the case of “consisting of”, the alternative embodiment excludes any additional compositions, materials, components, elements, features, integers, operations, and/or process steps, while in the case of “consisting essentially of”, any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being “on”, “engaged to”, “disposed”, “coated”, “connected to”, or “coupled to” another element or layer, it may be directly on, engaged, connected or coupled to the other component, element, or layer, or intervening elements or layers may be present. In contrast, when an element is referred to as being “directly on”, “directly engaged to”, “directly connected to”, or “directly coupled to” another element or layer, there may be no intervening elements or layers present. Other words used to describe the relationship between elements should be interpreted in a like fashion (e.g., “between” versus “directly between”, “adjacent” versus “directly adjacent”, etc.).

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as “first”, “second”, and other numerical terms when used herein may not imply a sequence or order unless clearly indicated by the context. Thus, a first step, element, component, region, layer or section discussed below may be termed a second step, element, component, region, layer or section without departing from the teachings herein.

Spatially or temporally relative terms, such as “before”, “after”, “inner”, “outer”, “beneath”, “below”, “lower”, “above”, “upper”, and the like, may be used herein for ease of description to describe one element or feature’s relationship to another element(s) or feature(s) as illustrated in the figures. Spatially or temporally relative terms may be intended to encompass different orientations of the device or system in use or operation in addition to the orientation depicted in the figures. As used herein, “top” means furthest away from the substrate, while “bottom” means closest to the substrate. Where a first layer is described as “disposed over”, “provided over”, or “deposited over” a second layer, the first layer is disposed further away from substrate. There may be other layers between the first and second layer, unless it is specified that the first layer is “in contact with”, “disposed on”, “provided on”, or “deposited on” the second layer.

The terms “on”, “appended to”, “affixed to”, “bonded to”, “adhered to”, or terms of like import means that the designated item, e.g., a coating, film or layer, is either directly connected to (superimposed on) the object surface, or indirectly connected to the object surface, e.g., through one or more other coatings, films or layers (superposed on).

“Substantially uniform coating” describes a film or coating formed on a surface of a substrate in which at least 80%, at least 90%, at least 95%, at least 98%, and at least 99% of the surface is covered. For example, the adhesive described herein may comprise a substantially uniform coating.

"Substantially uniform thickness" describes a film or coating formed on a surface of a substrate having thickness variation in at least one direction is less than 20%, less than 10%, less than 5%, less than 2% and less than 1%. For example, the adhesive described herein may comprise a substantially uniform thickness.

The COVID-19 pandemic has drastically changed our lives and imposed strong demands on health-care systems and medical supplies. Many experts agree that continued testing for COVID-19 may be a key part of our strategy for controlling further spread of the pandemic towards normalizing our socio-economic conditions. This may include testing a considerable portion of the U.S. population. To date, 2.6% of the U.S. population has been tested for SARS-CoV-2 virus, with about 16% of the U.S. population testing positive for SARS-CoV-2 infection. Recent studies suggest that the number of tests per day may increase 3 to 5 fold to better control the pandemic, and that the testing may continue until a viable vaccination approach is developed. However, the testing shortages have been hindering the ability to accelerate the testing efforts. Indeed, many hospital systems cannot adequately respond to the testing demands. One particular and critical shortage is the nasopharyngeal (NP) swabs used for testing. The shortage may be severe enough that each state, even each hospital, is bidding against each other, thereby increasing the prices per NP swabs by an order of magnitude from their original prices. Each of these hospital systems estimate they will need 1000s of swabs for the next 12 to 18 months as the epidemic continues. Accordingly, improved NP swabs and methods of manufacturing NP swabs to respond to the needs of both the local and state-wide hospitals, as well as other facilities (e.g., nursing homes) may be desirable.

The swabs according to the present invention may be used to collect samples for medical purposes, food and drug purposes, forensic purposes, and/or environmental purposes. The swabs may be used for testing for microorganism, such as viruses, aerobic, *Campylobacter*, Coliform, *E. coli*, Enterobacteriaceae, Lactic Acid Bacteria, *Listeria, Salmonella*, Yeast & Mold, and/or Staph *Aureus*, for example. The swabs may be used for testing blood, DNA, and other biological materials. Nasopharyngeal swabs may be used for testing of flu, COVID-19, SARS, and many other diseases. The tip of the swab may be inserted into a patient's nose or brushed along the back of the patient's throat to collect a sample of mucus. For the nasal sample, swabbing may occur in both nostrils to collect sufficient mucus for analysis. The sample may be analyzed to detect genetic material of the disease using a polymerase chain reaction (PCR) test, or certain proteins of the disease using an antigen test. Conventional swabs may include a tip that suffers from one or more of the following limitations: unable to capture sufficient sample (e.g., mucus), and retain it during retraction of the swab from the nose or throat; causes tissue damage during sample collection; made from materials other than FDA-approved materials; made from materials, in particular, materials used for the base, adhesive (and assisting chemicals), as well as fibers (i.e., flocking), that interfere with the test used to analyze the collected samples; may not be configured to be sterilizable with the FDA-approved methods (e.g., ethylene oxide, dry heat, autoclaving, and gamma irradiation); unable to secure the collected sample without a high degree of risk of contamination, and high usage costs.

The swabs according to the present invention have shown potential to collect and release significantly higher amount of biological sample than conventional swabs. The swabs according to the present invention may provide one or more of the following improvements relative to conventional swabs: reduce the rate of false negatives; increase the amount of sample collected; reduce the irritability by fabricating smaller swabs that can capture sufficient amount of sample; manufactured in a scalable (high throughput) and low-cost fashion; reproducibly flocked; and configured to be sterilized and individually packaged.

The swabs bodies (the rods) according to the present invention may be manufactured via injection molding, 3D printing, Swiss turning, and/or other plastic fabrication processes.

The swabs according to the present invention may be configured to be used with or without flocked fibers attached to the tip region to collect samples. The flocks may increase the amount of liquid collected/retained by the swab/flocking, respectively. However, sufficient amount of sample may be collected without the flocked fibers.

The present invention may provide scalable and rapid methods of manufacturing NP swabs to address the shortage of the NP swabs used for Covid-19 testing. The design of the NP swabs (before flocking) according to the present invention may comprise geometries to increase the effectiveness of the NP swabs by enabling them to collect a larger amount of sample. The design of the NP swabs base (the tip portion of the plastic rods) increase the surface area of the swab tips and provide regions for capturing samples (crevasses between the projections), both to facilitate better mucus attachment to the swab. Both of these positive effects may be further enhanced by uniform attachment of fibers to the tip portion surface, including both to the crevasses and the projections. The NP swabs according to the present invention may collect more than twice as much sample as conventional swabs.

A swab may comprise may have length of 15.24 cm (6 in.); a centrally located notch to facilitate breaking the swab and packaging the testing sample into a test tube; and a tip portion with adhered fibers. The base material (shank) may comprise polypropylene with specific dimensions, and the fibers at the tip may be attached by "flocking" them using adhesive with or without electrostatic charge (to align the fibers and to better attach them into the crevasses). The flocked tip may comprise nylon or rayon fibers and the fibers may be aligned. The flocked tip may be configured to collect sufficient biological (e.g., mucus, blood, vaginal fluid, saliva) samples and releasing it to the test tube with minimal adverse effect on the PCR results that assess the viral presence/load. The design and fiber attachment to the tip may contribute to their effectiveness. FDA classifies swabs as Class I, 510(k) exempt, in vitro diagnostic medical devices.

Referring to FIGS. 1 and 2A-C, a nasopharyngeal swab according to the present invention may comprise an absorbent tipped applicator device configured for medical purposes. The swab may comprise an absorbent nylon swab on an injection molded polystyrene rod. The shaft material may comprise high impact polystyrene ("HIPS") and the flocking material may comprise polyamide 6.6 fibers. The shaft may be free from other additives or substances except for incidental impurities.

Referring to FIG. 2A-C, the swabs according to the present invention may comprise an elongated body including a handle at one end and a tip at an opposed end. The tip may be flat-shaped and up to a few millimeters in radial dimension. The body may comprise a length from 2-20 cm in the axial direction, such as 3-18 cm and 6-16 cm. The body may comprise a thickness or diameter (generally speaking, a radial dimension) that is perpendicular to the central axis thereof (i.e., in the radial direction) from 0.5-5 mm, such as 1-3 mm and 1.5-2.5 mm. The tip may be covered with fibers. The tip may comprise a length from 0.5-8 cm, such as 1-5 cm. The tip region, including the tip and a region before the tip, may comprise a thickness or diameter (including the flocking) from 1-10 mm, such as 2-8 mm, and 2.5-5 mm. The diameter or thickness of the body may be smaller than or greater than the diameter or thickness of the tip. The body may comprise an intermediate weakened portion (e.g., a notch) to facilitate a selective breaking of the body at the intermediate position between the handle and tip to facilitate insertion of the tip into a container or tube for transport. The body may comprise a notch configured such that the tip and, optionally, a distal portion of the body, may be separated from the handle and stored in a test tube and the proximate portion of the body (e.g., the handle), may be disposed. The notch may be centrally positioned along the body. The swab may be manufactured by injection molding, 3D printing, Swiss turning, and/or other plastic manufacturing techniques. The fibers material attached to the swab tip portion by adhesive flocking and/or electrostatic flocking.

The tip according to the present invention may comprise a spherical end having a cross-sectional area configured to collect a sufficient amount of sample to be analyzed while minimizing patient discomfort during collection. The patient may experience discomfort when the tip is too wide to comfortably fit into the nasal cavity. The patient may experience discomfort or tissue damage may be experienced when the tip is too narrow and sharp. The straight tip swabs according to the present invention may be manufactured via 3D printing and injection molding and/or Swiss turning.

Referring to FIGS. 8A-F, the tip according to the present invention may comprise a honey-dipper type tip. The honey-dipper type tip may comprise a plurality of projections extending in the radial direction and/or axial direction. The projections may be configured to collect a sample (e.g., viscous liquids) with or without flocks. The density of the projections (number of projections per unit area), diameter of the projections (along the radial direction of the swab), width of the projections (along the axial direction of the swab), and/or diameter of the core of the tip may each independently increase, decrease, or remain constant along the axial direction. A thinner core may provide increased flexibility to the swab relative to a swab having a thicker core. The honey-dipper type tip swabs according to the present invention may be manufactured via injection molding, 3D printing, Swiss turning, and/or other plastic manufacturing methods. For example, the tip portions may be manufactured via 3D printing and co-molded (as inserts) when injection molding the swabs.

Referring to FIGS. 7A-E, the projections may comprise a waveform pattern or pulse. The waveform pattern or pulse may comprise a sine wave, a square wave, a triangle wave, a sawtooth wave, a semicircle wave, a curved wave, and combinations thereof. The waveform pattern may be characterized by frequency, amplitude, and phase. The amplitude and frequency of the projections may vary depending upon the specific application for the swab and materials used. For example, the swab may comprise sinusoidal-shaped roughing projections having a greater amplitude than the amplitude of the sinusoidal-shaped moderate projections whereby the sinusoidal-shaped roughing projection agitate/stimulate hair follicles in the nasal cavity of the patient so as to loosen the mucus that may be collected by the sinusoidal-shaped moderate projections and/or flock. The result of the agitation/stimulation of the hair follicles by the sinusoidal-shaped roughing projections may increase the amount of material collected by the swab. The frequency, amplitude, phase, and tilt for each of the plurality of the projections may be the same as or different from the frequency, amplitude, phase, and tilt of another one of the plurality of the projections.

As used herein, the term "sinusoidal projections" and "helical projections" refers to the radial portions of the tip that contact and/or collect the sample, in which the projections have a geometric shape comprising a sinusoidal curve component and a helical curve component. Therefore, it is understood that the sinusoidal and helical projections of the tip may be formed by the alignment of the sinusoidal and helical projections of individual projections positioned along the tip. In addition, it is understood that the sinusoidal and helical projection described herein comprise a combined sinusoidal and helical geometric shape within generally acceptable tolerances in the injection molding and/or 3D printing industries.

The tip portion according to the present invention may create a mathematical design model that may be used to manufacture tips having sinusoidal and helical projections that together form a swab having a sinusoidal and helical collection surface. The mathematical design model defines a collection surface having a three-dimensional complex geometry comprising a combined sinusoidal curve component and helical curve component.

Similarly, the axial cross-section of the swab at the tip region may comprise a circular shape, a semi-circular shape, a flower-petal shape, a closed-curve shape, and combinations thereof.

The waveform pattern may comprise helical pattern comprising a sinusoidal waveform. Referring to FIGS. 9A-G, the tip according to the present invention may comprise a helical tip. The helical tip may be configured to collect a sample with or without flocks. The helical tip may be configured to collect a sample via the grooves when the swab is rotated (i.e., an Archimedes' screw-motion). The tip may comprise a core having a diameter the same or less than the handle to provide stability and/or flexibility to the tip. The density of the helices (i.e., turns per unit area), diameter of the helices (along the radial direction of the swab), length of the helices (along the axial direction of the swab), pitch of the helical curve (helical rotations per length) and/or diameter of the core of the tip may each independently increase, decrease, or remain constant along the axial direction. The tip may comprise one of a single helix and a multiple-helix (e.g., one with changing diameter or pitch along the axial direction). The helical tip swabs according to the present invention may be manufactured via injection molding, 3D printing, and/or Swiss turning. For example, the tip may be molded seamlessly in a one-piece mold and removed from the mold by unscrewing the tip when the tip lacks an increasing cross section towards the end of the it. In another example, the tip portions may be manufactured via 3D printing and co-molded (as inserts) when injection molding the swabs.

Referring to FIGS. 4A-G, the swabs according to the present invention may comprise one or more of the following designs: a tip portion comprising the projections up to 300 mm, such as from 0.5-300 mm, 1-150 mm, and 50-100 mm; a tip-shaft diameter up to 10 mm, such as 0.1-10 mm and 0.2-5 mm; a projection fillet radius up to 2 mm, such as up to 1 mm; to enable machining of injection molding molds; a projection wall angle greater than 0° and less than 180°, such as 0.1-179.9°, (such that the projection does not comprise a flat geometry lacking the projections); a projection diameter up to 100 times the tip-shaft diameter, such as 0.5-50, 1-25, 25-50, and 50-100 times the tip-shaft diameter; a projection distance up to 30 mm, such as 0.2-15 mm, 1-7 mm, and 7-15 mm; as shaft diameter up to 40 times the tip-shaft diameter, such as 0.2-20, 1-10, and 20-40 the tip-shaft diameter; a notch diameter less than 1 times the shaft diameter, such as 0.01-0.99, 0.01-0.09, and 0.1-0.99 times the shaft diameter; a notch fillet radius up to 10 mm, such as 0.05-5 mm, 0.1-5 mm, and 5-10 mm; a notch length up to 10 mm, such as 0.05-5 mm, 0.01-5 mm, and 5-10 mm; a transition-1 fillet radius up to 200 mm, such as up to 100 mm, and 1-100 mm; a middle section diameter from the shaft diameter to the tip-shaft diameter; a transition-1 length up to 400 mm, such as up to 200 mm, and 1-200 mm; a transition-2 length up to 200 mm, such as up to 100 mm, and 1-100 mm; a tip transition length up to 200 mm, such as up to 100 mm, and 1-100 mm; and a tip transition fillet radius up to 100 mm, such as up to 50 mm and 1-50 mm.

For example, the swab according to the present invention may comprise a total length of 152.4 mm comprising a handle having a length of 69.9 mm and a diameter of 2.54 mm, an intermediate portion having a length of 82.5 mm and a proximal portion having a diameter of 2.54 mm and a distal portion having a diameter of 1.18 mm, and a tip having a length of 23.5 mm and a diameter of 1 mm. The swab includes a first transition zone from the handle to the intermediate portion having a length of 0.775 mm and a diameter of 1.65 mm. The intermediate zone includes a second transition zone form the proximal portion to the distal portion having a length of about 2.54 mm and a gradient diameter decreasing from 2.54 mm to 1.18 mm. The intermediate zone includes a third transition zone having a length of 0.49 mm and a gradient diameter decreasing from 1.18 mm to 1 mm. The swab includes a fourth transition zone from the intermediate portion to the tip having a length of about 1 mm a gradient diameter increasing from 1 mm to 2.75 mm. The tip may comprise 11-13 projections, a base projection and an end projection, and may be spaced 1.44 mm, 1.55 mm, or 1.68 mm apart, respectively, from the adjacent projection relative to the central axis of each projection orthogonal to a longitudinal axis of the swab. Each projection may have a diameter of 2.75 mm and a pitch of 75° when relative to the surface of the swab. The projection may comprise an proximal curved edge and a distal curved edge each having a length of 0.254 mm. The projection may comprise a curved transition zone from the projection to the surface of the swab having a length of 0.254 mm.

Figure 10:
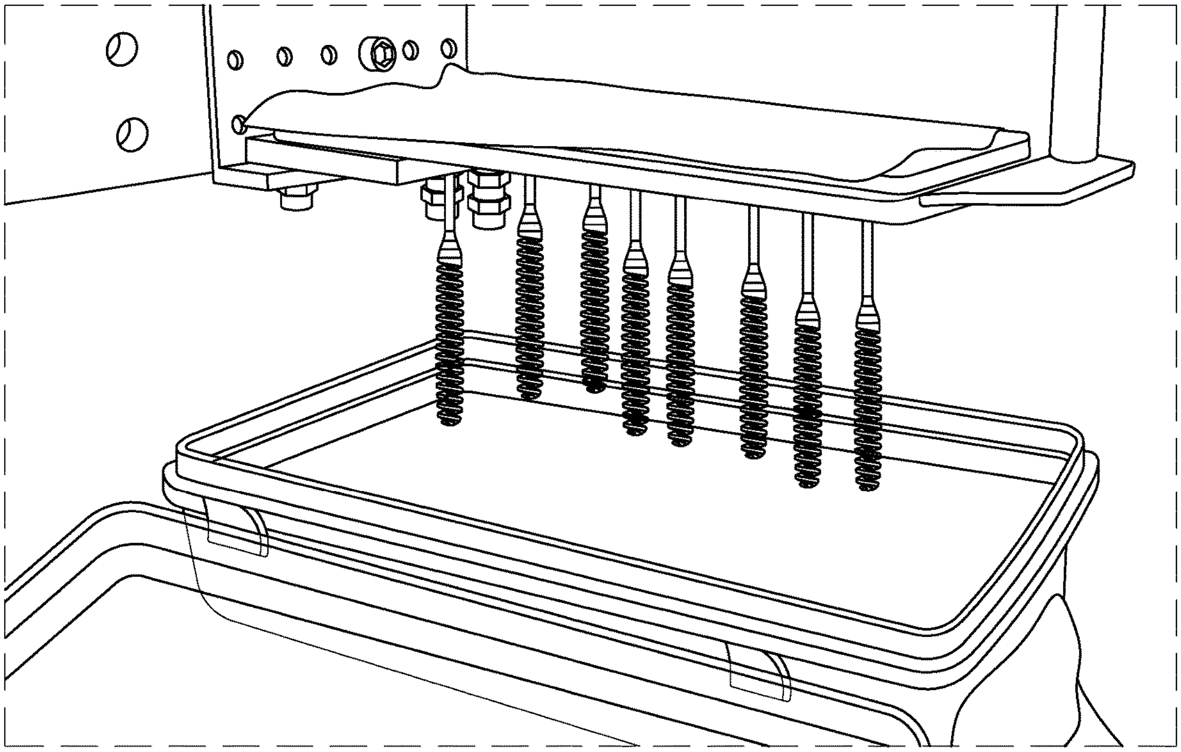
FIG. 10 shows a method of manufacturing swabs according to the present invention comprising contacting the swab and an adhesive via dipping to apply the adhesive to the surface of the swab.

The swabs according to the present invention may be coated with a thin and uniform layer of an adhesive (e.g., a light cured adhesive and a heat cured adhesive). The adhesive may comprise, e.g., and epoxy resin including light and/or heat cured acrylic-based, polyurethane-based, polyamide-based, polyester-based, vinyl-based and/or two-part epoxy adhesives, silicones, cyanoacrylates, polyurethanes and/or latex adhesives. The adhesive may be water-based. Referring to FIG. 10, the swab may be supported by a holder and dipped into an adhesive bath for up to 1 minute, such as 5 seconds, for example, and retracted. In another example, the adhesive may be sprayed (in aerosol form) onto the projections. Any excess adhesive may be removed from the projections using compressed air.

Figure 11:
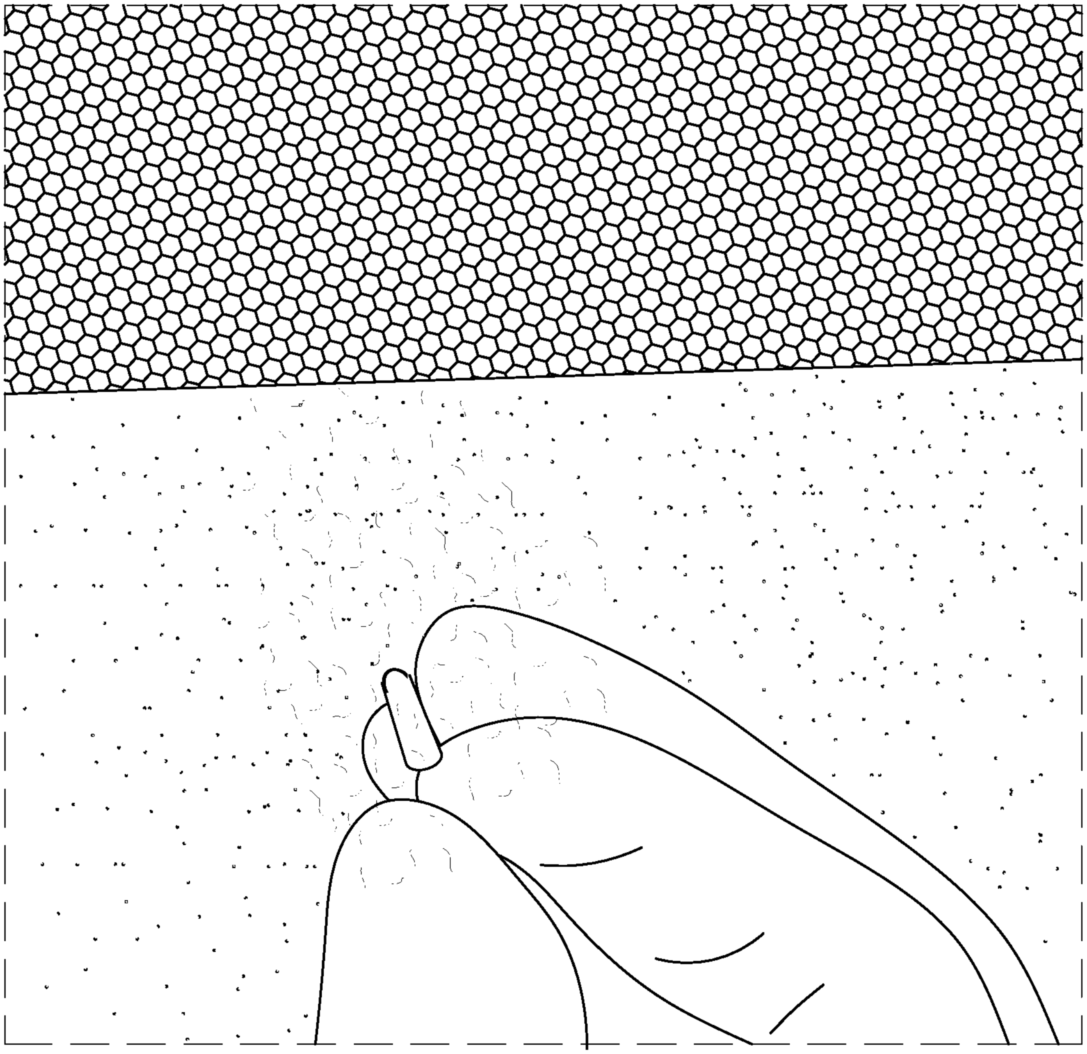
FIG. 11 shows a method of manufacturing swabs according to the present invention comprising contacting the swab coated with the adhesive and nylon and/or rayon fibers to flock the fibers to the adhesive to the surface of the swab.

The flocking material may comprise cut fibers with specific length and density (weight per length), including synthetic or artificial materials, e.g., nylon, rayon, polyester, polyamide, carbon fiber, alginate, and natural materials, e.g., cotton and silk, or mixtures thereof. The flocking material may be hydrophilic. The flocking process may utilize an electrostatic field to deposit the flocking material in an ordered manner, perpendicular to the surface of the tip of the swab rod, which has been previously coated with adhesive, such as by immersion or spraying, for example. Referring to FIG. 11, the flocking may be applied to the surfaces coated with adhesive via an air assisted spray gun. The tips may be rotated under a stream of flock fibers for a time sufficient to cover the tip with the fibers, such as 20 seconds, for example. In spray-gun application, subsequent to applying adhesive, fibers may be blown over the plastic body, with or without rotating or changing the orientation of the plastic body, to attach the fibers onto the tip portion uniformly.

The flocking material may comprise of uniform thickness from 0.1-3 mm, a length from 0.6-3 mm, such as 0.75-1 mm, a yarn count from 1-10 Dtex (i.e., the weight in grams per 10,000 linear meters of a single fiber), such as 1-4, 2-5, 1.7-3.3, 5-10, and 6-8 Dtex, a surface density from 50-500 fibers per $mm^2$, such as 100-200, 50-300, and 250-500 fibers per $mm^2$, and/or an absorbance capacity of at least 0.5 microliters per $mm^2$, such as at least 0.6 microliters per $mm^2$, at least 0.7 microliters per $mm^2$, and at least 0.75 microliters per $mm^2$. The amount of flocking material deposited on the tip to form the flocked layer may be selected on the basis of the type of fiber and the desired layer characteristics of thickness and fineness to collect a desired amount of sample, such as, 100 microliters of mucus. The swabs may collect 5-1000 microliters of sample, such as 10-500 microliters, 50-200 microliters, 35-200 microliters, 80-120 microliters, 40 microliters, 50 microliters, 60 microliters, 70 microliters, 80 microliters, 90 microliters, 100 microliters, 120 microliters, 130 microliters, 140 microliters, 150 microliters, 160 microliters, 170 microliters, 180 microliters, and 190 microliters without causing damage or substantial discomfort to the patient during collection.

Figure 12:
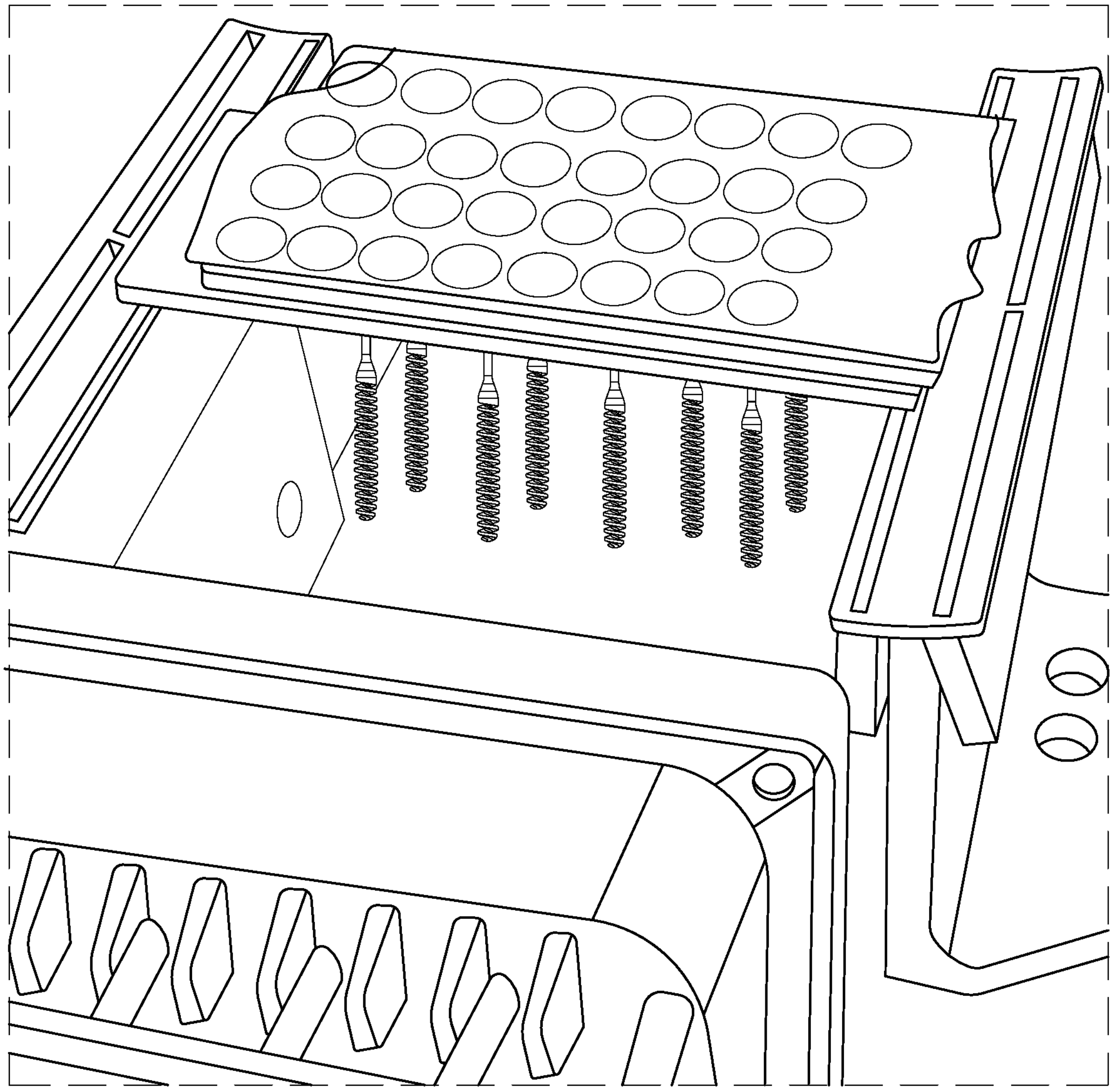
FIG. 12 shows a method of manufacturing swabs according to the present invention comprising curing the swab coated with the adhesive and flock via ultraviolet curing lamps.
Figure 13A:
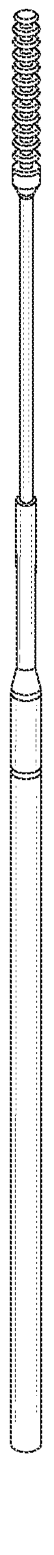
FIGS. 13A-H show swabs according to the present invention.
Figure 13B:
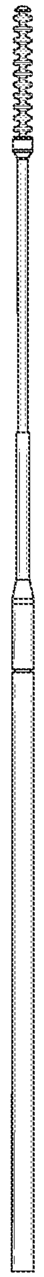
Figure 13C:
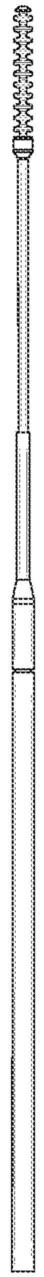
Figure 13D:
Figure 13E:
Figure 13F:
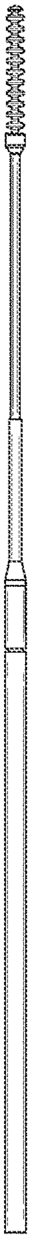
Figure 13G:
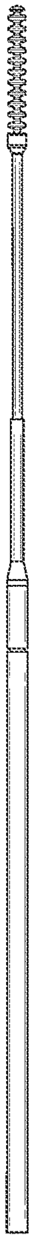
Figure 13H:
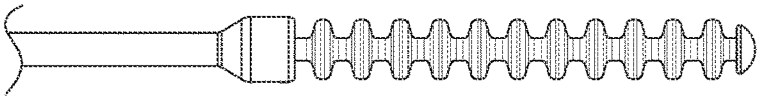
Figure 14A:
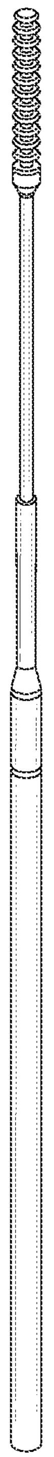
FIGS. 14A-H show swabs according to the present invention.
Figure 14B:
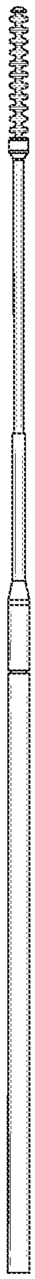
Figure 14C:
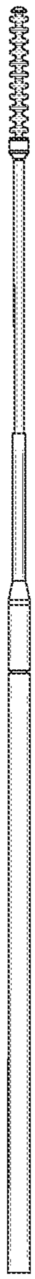
Figure 14D:
Figure 14E:
Figure 14F:
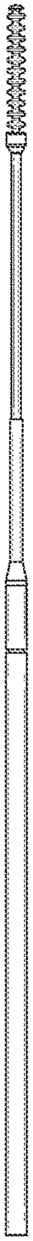
Figure 14G:
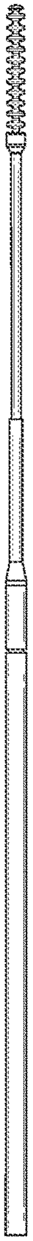
Figure 14H:
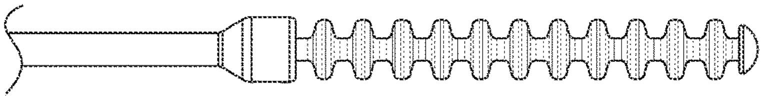
Figure 15A:
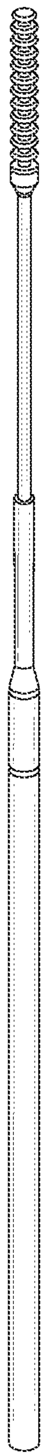
FIGS. 15A-H show swabs according to the present invention.
Figure 15B:
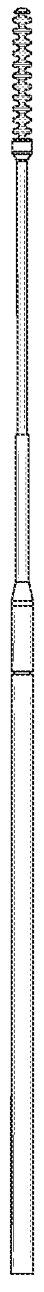
Figure 15C:
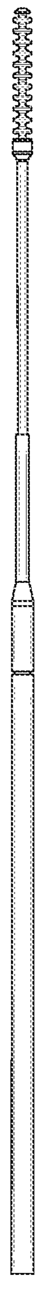
Figure 15D:
Figure 15E:
Figure 15F:
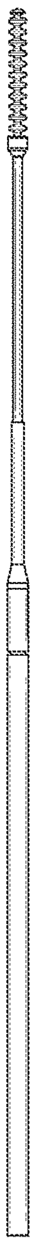
Figure 15G:
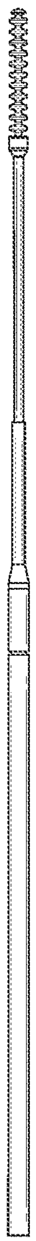
Figure 15H:
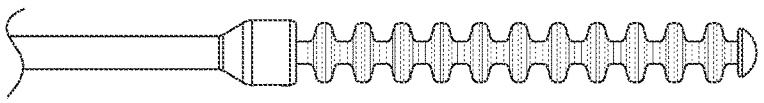

Referring to FIG. 12, the light cured adhesive may be cured via LED UV curing lamps operating at 365 nm or 405 nm, depending on the adhesive) for 5 min per side (2 sides). In another example, the heat cured adhesive may be cured by heating the adhesive to 65° C. for 15 min. The flocked swab may be dried by exposing it to a source of heat or radiofrequency.

The swabs according to the present invention may be used to collect biological samples from oral, nasal, ocular, rectal, urethral, or vaginal orifices of a mammal, such as a human, or patient or for veterinary purposes. For example, the method of collecting a biological sample from a patient may comprise contacting a swab as described herein with a source of biological material such that a sample of the material is retained by the swab. A method for collecting a sample with a swab, the method comprising the steps of: collecting a sample by contacting a projection according to the present invention and/or a layer of fibers of a flocking materials; storing and transporting a quantity of the collected sample; and releasing a quantity of the collected sample to be analyzed from projections and/or fibers. The method may comprise collecting and transferring DNA samples, RNA samples, and/or cells comprising samples of DNA or RNA. The method may comprise the step of analyzing said quantity of specimen after releasing said specimen from said layer of fibers.

The swabs according to the present invention may comprise a component of a collection, transport, culture and/or transport kit or device wherein additional specimen handling containers and/or devices may be included and the swab may be configured to be integrated with such other container and/or devices to provide one or more of specimen retention, integrity and/or sterility.

Example

The swabs as well as methods of making and using the same described herein may be better understood when read in conjunction with the following representative examples. The following examples are included for purposes of illustration and not limitation.

The nasopharyngeal swab according to the present invention are compared to conventional swabs for the following characteristics: (1) gel capture, (2) retrieval of specimens from the nasopharynx, (3) impact on COVID test efficiency, (4) breakability, and (5) sterilization. The details of are provided below.

Gel Capture Efficiency Evaluation.

Figure 16:
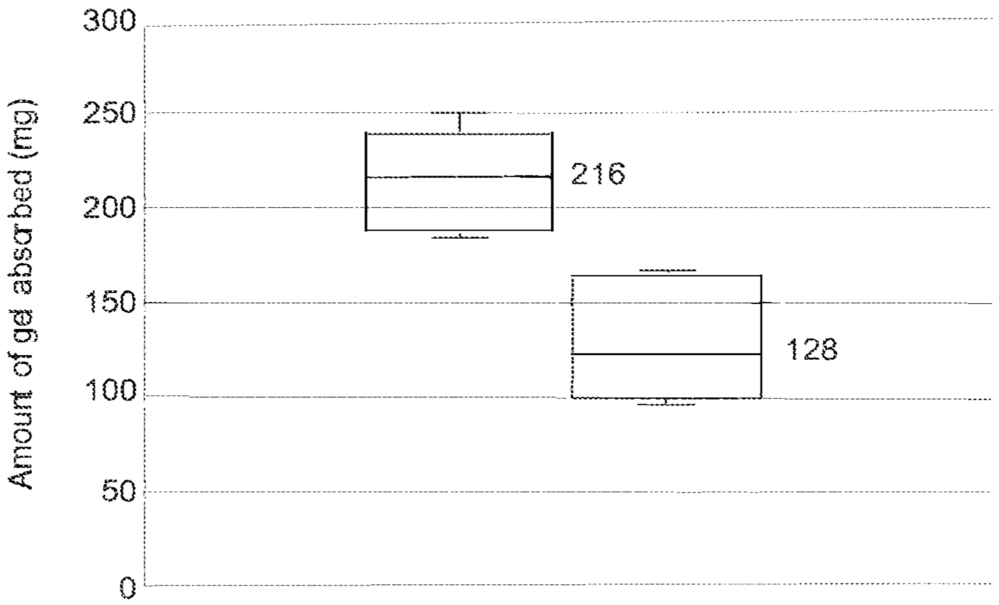
FIG. 16 depicts swab test results.

Studies were conducted to evaluate how much gel each swab could capture as compared to a conventional NP swab. For this purpose, a surrogate mucus sample (Sterile Lubricating Jelly, Medline) was placed on a petri dish and swabs were used to sample/absorb the gel. The weight of the gel absorbed by each swab is (to the 0.001 g resolution) were used as the metric. Referring to FIG. 16, each type of swab was tested in two separate tests and in triplicate for each test. The swab according to the present invention collected 216 mg of gel on average, with a standard deviation of 23.6 mg, minimum of 185 mg, and maximum of 251 mg. The conventional swab collected 128 mg of gel on average, with a standard deviation of 28.9 mg, minimum of 95 mg and maximum of 163 mg. In other words, the swab according to the present invention collected 1.7 times more gel on average than the commercial swabs, with a lower standard deviation.

Nasopharyngeal Specimen Retrieval Studies.

The swab according to the present invention was tested for specimen retrieval efficiency using high fidelity simulation manikins with colored mucus-like gels and multiple medical personnel. These studies found that the swabs were very effective in absorbing simulated specimen samples from the manikin's nasopharynx at least at levels seen with the commercial swab, and in many cases, more than the commercial swabs as indicated by the amount of colored gel retrieved.

COVID Test Efficiency.

COVID test efficiency analyses were performed to ensure that the swab according to the present invention's base material (e.g., high-impact polystyrene), nylon fibers (e.g., polyamide 6.6), and the adhesive used to attach the flocks to the swab tips did not interfere with the SARS-CoV-2 RT-PCR testing, i.e., providing the same results as the commercial swabs. As noted previously, the swabs according to the present invention uses the same base material and flocking fiber material as those of the commercial swabs. The sample swabs and commercial swabs were similarly exposed to known positive and negative human COVID-19 serum samples and placed in test tubes containing sterile media overnight to evaluate testing efficiency. The sample swab flocking material was observed to be stable under these conditions. Subsequently, the specimens were extracted from both the prototype and commercials swabs and were then tested on several RT-PCR commercial laboratory platforms. All sample swabs performed similar to commercial swabs producing the same positive or negative COVID-19 results for all human serum samples.

Mechanical Flexibility and Breakability.

The overall mechanical flexibility and notch breakability of the swabs is also tested. This was done in side-by-side comparisons with commercially available swabs by medical personnel to determine the ability to place the swab's appropriate length in media filled test tubes once specimens are collected in the field. The swabs according to the present invention were extremely flexible and unbreakable except at the notch giving confidence that in clinical use, the swab would not break unless intended to do so by the user at the notch point only after specimen collection.

Sterilization Testing.

The swab according to the present invention are evaluated the sterilization. Sample swabs were placed in sterile media both with and without antibiotic and antifungal agents overnight and subsequently cultured in our microbiology laboratory to determine sterility. No organisms grew from swabs placed in either media type with the packaging, and the sterilization process was determined to be effective. Lastly, the sterile sample swabs were subjected to the same positive and negative human COVID-19 serum samples using the same protocol as above. Again, the flocking material was observed to stabilize after sterilization, and identical results for both positive and negative COVID-19 human serum samples were observed when compared to the commercial swabs.

The present invention is directed to the following aspects:

Aspect 1. A device to collect a biological sample, the device comprising an elongated rod comprising a core and terminating in a tip; and a plurality of projections extending in a radial direction from a surface of the core; wherein the plurality of projections comprises a geometric pattern.

Aspect 2. The device of aspect 1 comprising a layer of fibers disposed on a surface of at least one of the plurality of projections by flocking.

Aspect 3. The device of any of the forgoing aspects, wherein at least one of the plurality of projections is roughened to facilitate fiber attachment and/or sample collection.

Aspect 4. The device of any of the forgoing aspects, wherein the geometric pattern comprises a curved geometric pattern selected from a sinusoidal pattern, a circular arc pattern, and/or a helical pattern.

Aspect 5. The device of any of the forgoing aspects, wherein at least one of the plurality of projections comprises a cross-sectional profile selected from a closed shape, a pedal curve, a polygon, a circle, a cylinder, an ellipsoid, a parabola, a hyperbola, and combinations thereof.

Aspect 6. The device of any of the forgoing aspects, wherein at least one of the plurality of projections comprise an amplitude (in the axial direction) from 0.1-10 times (e.g., 0.1-1, 2-4, 4-6, 6-8, 8-10, 1-5, and 5-10) a diameter of the core relative to a surface of the core; and/or a frequency (number of projections) from 2-25 (e.g., 2-8, 4-6, 8-18, 10-16, 12-14, 18-25, and 20-24) along the longitudinal axis of the tip; and/or a tilt from greater than 0 up to 90° (e.g., 15-45°, 30-60°, and 45-90°) relative to the surface of the core.

Aspect 7. The device of any of the forgoing aspects, wherein at least one of the plurality of projections comprise a helical pattern having a pitch from greater than 0 up to 90° (e.g., 15-45°, 30-60°, and 45-90°) relative to the surface of the core.

Aspect 8. The device of any of the forgoing aspects, wherein at least one of the plurality of projections comprises an amplitude, tilt, thickness and/or pattern different from another one of the plurality of projections.

Aspect 9. The device of any of the forgoing aspects, wherein the amplitude of plurality of projections decreases from a distal end of the tip to a proximal end of the tip.

Aspect 10. The device of any of the forgoing aspects, wherein the amplitude of the plurality of projections decreases from a central portion of the tip towards at least one of a distal end of the tip and a proximal end of the tip.

Aspect 11. The device of any of the forgoing aspects, wherein the projection at the distal end of the tip comprises one of a flat surface and a curved surface extending in an axial direction along the core.

Aspect 12. The device of any of the forgoing aspects, wherein the plurality of projections comprises a helical pattern extending from a distal portion of the tip to a proximal portion of the tip.

Aspect 13. The device of any of the forgoing aspects, wherein the helical pattern comprises at least one of a cylindrical helix, a conic helix, a circular helix, and a slant helix; and a right-handed helix and/or a left-handed helix.

Aspect 14. The device of any of the forgoing aspects, wherein the distal end of the tip comprises a spherical shape having a diameter greater than a central portion of the tip.

Aspect 15. The device of any of the forgoing aspects characterized by an average weight gain (in mg) greater than a swab lacking the plurality of projections.

Aspect 16. A device of any of the forgoing aspects to collect a sample comprising an elongated rod having a handle and terminating in a tip; and a core and a plurality of projections extending in a radial direction from a surface of the core.

Aspect 17. A device of any of the forgoing aspects, wherein the plurality of projections may individually comprise a curved geometric pattern, such as a sinusoidal pattern, a circular arc pattern, and/or a helical pattern, and/or a waveform pattern, such as, a sine wave, a square wave, a triangle wave, a sawtooth wave, and combinations thereof.

Aspect 18. A device of any of the forgoing aspects comprising a layer of fibers disposed on a surface of the projections by flocking.

Aspect 19. A device of any of the forgoing aspects configured to collect a sample with or without flocked fibers.

Aspect 20. A method of making a device of any of the forgoing aspects to collect a sample via injection molding, 3D printing, Swiss turning, and/or other plastic fabrication processes to generate the device comprising the plurality of projections. The method may comprise sterilizing and/or individually packaging the device.

Aspect 21. A method of making a device of any of the forgoing aspects comprising injection molding the elongated rod and the plurality of projections; applying an adhesive coating to at least one of the plurality of projections, disposing flocking material to at least one the coated projections, and curing the device coated with the adhesive and flocking material. The method may comprise sterilizing and/or individually packaging the device.

Aspect 22. A method of making a device of any of the forgoing aspects comprising 3D printing the tip comprising a plurality of projections; co-molding the tip and a handle via injection molding to generate the elongated rod; applying an adhesive coating to at least one of the plurality of projections, disposing flocking material to at least one the coated projections, and curing the device coated with the adhesive and flocking material. The method may comprise sterilizing and/or individually packaging the device.

Aspect 23. A method of using the device of any of the forgoing aspects comprising collecting a biological sample from a patient or object by contacting the swab and a source of material such that a sample of the material is retained by the swab. The patient may be a human, small animal (e.g., dogs, cats, and other companion animals/household pets such as hamsters and gerbils), laboratory animal (e.g., bovines, porcine species, felines, canines, rodents, and exotic animals), or large animal (e.g., livestock and other large farm animals, as well as equine species and large reptiles). The swab be used to collect biological samples from oral, nasal, ocular, rectal, urethral, or vaginal orifices of the patient. The object may be a surface or fluid potentially contaminated with pathogens and/or microbes.

Aspect 24. A method of using the device of any of the forgoing aspects comprising collecting a sample by contacting at least one of the plurality of projections and/or a layer of fibers of a flocking materials disposed on at least one of the plurality of projections; storing and transporting a quantity of the collected sample; and releasing a quantity of the collected sample to be analyzed from the projections and/or fibers. The method may comprise rotating the swab in a direction of the projections (e.g., for a right-handed helix or a left-handed helix) to collect the sample. The method may comprise the step of analyzing the quantity of the sample after releasing the sample from the projection and/or fibers.

Aspect 25. A device of any of the forgoing aspects comprising a component of a collection, transport, culture and/or transport kit or device and/or container and/or devices configured to be integrated with the swab and/or tip to provide one or more of sample retention, integrity and/or sterility.

All documents cited herein are incorporated herein by reference, but only to the extent that the incorporated material does not conflict with existing definitions, statements, or other documents set forth herein. To the extent that any meaning or definition of a term in this document conflicts with any meaning or definition of the same term in a document incorporated by reference, the meaning or definition assigned to that term in this document shall govern. The citation of any document is not to be construed as an admission that it is prior art with respect to this application.

While particular embodiments have been illustrated and described, it would be obvious to those skilled in the art that various other changes and modifications may be made without departing from the spirit and scope of the invention. Those skilled in the art will recognize or be able to ascertain using no more than routine experimentation, numerous equivalents to the specific apparatuses and methods described herein, including alternatives, variants, additions, deletions, modifications and substitutions. This application including the appended claims is therefore intended to cover all such changes and modifications that are within the scope of this application.

What is claimed is:

1. A swab to collect and retain a liquid biological sample, the swab comprising:

an elongated, plastic rod comprising a handle and a core terminating in a tip;

wherein the core comprises a longitudinal direction and a lateral direction;

wherein the core comprises a plurality of projections intermediate the handle and the tip to collect and retain the liquid biological sample;

wherein the handle, core, tip and plurality of projections comprise a unitary, continuous, plastic material;

wherein each of the plurality of projections extends in the lateral direction from a surface of the core;

wherein each of the plurality of projections comprises an amplitude from 0.1 to 10 times a diameter of the core, and a tilt from greater than 0° up to 90° relative to the longitudinal direction of the core, wherein the plurality of projections comprises a frequency from 2 to 25 along the longitudinal direction of the core, and wherein the plurality of projections comprise a geometric pattern selected from a square wave, a triangle wave, a sawtooth wave, a semicircle wave, a curved wave, and combinations thereof.

2. The swab of claim 1, wherein the plurality of projections comprises 8 to 18 projections.

3. The swab of claim 1, wherein the elongated, plastic rod comprises a diameter in the lateral direction from 0.5 mm to 5 mm, and a length in the longitudinal direction from 2 cm to 20 cm.

4. The swab of claim 1, wherein the core comprises a diameter from 1 mm to 10 mm, wherein the amplitude of each of the plurality of projections is from 0.1 mm to 100 mm, and wherein a projection distance of each of the plurality of projections is from 0.2 mm to 15 mm.

5. The swab of claim 1, wherein the amplitude for each of the plurality of projections is constant.

6. The swab of claim 1, wherein the amplitude for the plurality of projections is variable.

7. The swab of claim 1, wherein the tilt for each of the plurality of projections is constant.

8. The swab of claim 1, wherein the tilt for the plurality of projections is variable.

9. The swab of claim 1, wherein the tip comprises one of a flat surface and a curved surface.

10. The swab of claim 1, wherein the geometric pattern is semicircle wave.

11. The swab of claim 1, wherein the plurality of projections comprises a helical pattern.

12. The swab of claim 11, wherein the helical pattern comprises at least one of a cylindrical helix, a conic helix, a circular helix, and a slant helix.

13. The swab of claim 1, wherein the plurality of projections collects and retains 5-1000 microliters of the liquid biological sample when contacted with the liquid biological sample.

14. The swab of claim 1 characterized by a capture efficiency greater than a swab lacking the plurality of projections recited in claim 1.

15. The swab of claim 1 characterized by a retrieval efficiency greater than a swab lacking the plurality of projections recited in claim 1.

16. The swab of claim 1 characterized by rotational symmetry along the longitudinal direction.

17. The swab of claim 1, wherein the swab comprises a nasal swab, wherein the swab lacks flocking, wherein the plurality of projections comprises 8 to 18 projections, wherein the amplitude for each of the plurality of projections is constant, wherein geometric pattern is semicircle wave, wherein the plurality of projections comprises a helical pattern, wherein the tip comprises one of a flat surface, wherein the swab is characterized by rotational symmetry along the longitudinal direction, and wherein the plurality of projections collects and retains 5-1000 microliters of the liquid biological sample when contacted with the liquid biological sample.

18. A swab to collect and retain a liquid biological sample, the swab comprising:

an elongated, plastic rod comprising a handle and a core terminating in a tip;

wherein the core comprises a longitudinal direction and a lateral direction;

wherein the core comprises a plurality of projections intermediate the handle and the tip to collect and retain the liquid biological sample;

wherein the handle, core, tip and plurality of projections comprise a unitary, continuous, plastic material;

wherein each of the plurality of projections extends in the lateral direction from a surface of the core;

wherein each of the plurality of projections comprises an amplitude from 0.1 to 10 times a diameter of the core, and a tilt from greater than 0° up to 90° relative to the longitudinal direction of the core, wherein the plurality of projections comprises a frequency from 2 to 25 along the longitudinal direction of the core, and wherein the plurality of projections comprise a geometric pattern selected from a square wave, a triangle wave, a sawtooth wave, a semicircle wave, a curved wave, and combinations thereof, and a layer of flocking disposed on at least a portion of the plurality of projections.

* * * * *